(12) United States Patent
Maale et al.

(10) Patent No.: US 11,313,787 B2
(45) Date of Patent: Apr. 26, 2022

(54) SENSOR DEVICE FOR BIOSENSING AND OTHER APPLICATIONS

(71) Applicant: Zyvex Labs, LLC, Richardson, TX (US)

(72) Inventors: Gerhard Maale, Dallas, TX (US); Rahul Saini, Allen, TX (US); John Neal Randall, Richardson, TX (US)

(73) Assignee: ZYVEX LABS, LLC, Richardson, TX (US)

(*) Notice: Subject to any disclaimer, the term of this patent is extended or adjusted under 35 U.S.C. 154(b) by 128 days.

(21) Appl. No.: 16/933,348

(22) Filed: Jul. 20, 2020

(65) Prior Publication Data

US 2020/0348289 A1 Nov. 5, 2020

Related U.S. Application Data

(63) Continuation of application No. 15/263,872, filed on Sep. 13, 2016, now abandoned.
(Continued)

(51) Int. Cl.
*G01N 21/21* (2006.01)
*G01N 21/47* (2006.01)
(Continued)

(52) U.S. Cl.
CPC ........ *G01N 21/211* (2013.01); *G01N 21/47* (2013.01); *G01N 33/525* (2013.01);
(Continued)

(58) Field of Classification Search
CPC .................................................. G01N 21/211
(Continued)

(56) References Cited

U.S. PATENT DOCUMENTS

| 4,815,843 | A | 3/1989 | Tiefenthaler et al. |
| 9,552,985 | B2 * | 1/2017 | Inoue ............ C01G 15/00 |

(Continued)

FOREIGN PATENT DOCUMENTS

| CN | 1531650 | 9/2004 |
| CN | 103995020 | 8/2014 |

(Continued)

OTHER PUBLICATIONS

International Searching Authority, Notification of Transmittal of the International Search Report and the Written Opinion of the International Search Authority issued in Application No. PCT/US2016/051467, dated Dec. 28, 2016, 9 pages.
(Continued)

*Primary Examiner* — Tarifur R Chowdhury
*Assistant Examiner* — Omar H Nixon
(74) *Attorney, Agent, or Firm* — Haynes and Boone, LLP

(57) ABSTRACT

A sensor suitable for detecting specific analytes, a method for manufacturing the sensor, and a method for using the sensor in a diagnostic procedure provided. In an embodiment, the sensor device includes a substrate, a dielectric layer disposed on the substrate, and a probe layer disposed on the dielectric layer. The probe layer is configured to react with an analyte. The reaction may include: binding with the analyte, undergoing a change in a chemical property of the probe layer, or undergoing a change in a structural property of the probe layer. In examples, an attribute of the dielectric layer is configured to identify the device during a process that determines whether the probe layer has reacted with the analyte.

18 Claims, 10 Drawing Sheets

Related U.S. Application Data

(60) Provisional application No. 62/220,119, filed on Sep. 17, 2015.

(51) Int. Cl.
  *G01N 33/52* (2006.01)
  *G01N 33/543* (2006.01)
  *C12Q 1/68* (2018.01)
  *G01N 21/45* (2006.01)
  *G01N 27/327* (2006.01)

(52) U.S. Cl.
  CPC ......... *G01N 33/54306* (2013.01); *C12Q 1/68* (2013.01); *G01N 21/45* (2013.01); *G01N 27/3275* (2013.01); *G01N 33/54373* (2013.01)

(58) Field of Classification Search
  USPC ........................................... 356/369
  See application file for complete search history.

(56) References Cited

U.S. PATENT DOCUMENTS

| | | | |
|---|---|---|---|
| 10,055,530 B1* | 8/2018 | Sinivaara | B33Y 50/02 |
| 2002/0135781 A1* | 9/2002 | Singh | G01B 11/26 356/601 |
| 2004/0070764 A1 | 4/2004 | Fujimura et al. | |
| 2005/0199822 A1 | 9/2005 | Saini et al. | |
| 2007/0105029 A1* | 5/2007 | Ausschnitt | G03F 7/70633 430/30 |
| 2007/0132043 A1 | 6/2007 | Bradley et al. | |
| 2008/0113446 A1 | 5/2008 | Wark et al. | |
| 2009/0116020 A1* | 5/2009 | Wu | G01N 33/54373 356/445 |
| 2009/0221096 A1 | 9/2009 | Torres | |
| 2011/0058172 A1* | 3/2011 | Moon | G01N 33/54306 356/417 |
| 2011/0171072 A1 | 7/2011 | Dave | |
| 2013/0071289 A1 | 3/2013 | Knoll | |
| 2013/0261010 A1* | 10/2013 | Bailey | G01N 33/54326 506/9 |
| 2013/0295688 A1 | 11/2013 | Bailey et al. | |
| 2013/0323858 A1 | 12/2013 | Abdulhalim | |

FOREIGN PATENT DOCUMENTS

| | | |
|---|---|---|
| EP | 0353937 A1 | 7/1990 |
| EP | 1724584 A1 | 11/2006 |
| EP | 2693202 A1 | 2/2014 |
| WO | 200231478 A2 | 4/2002 |
| WO | 2006048660 A1 | 5/2006 |
| WO | 2015054515 A1 | 4/2015 |

OTHER PUBLICATIONS

European Patent Office, Extended European Search Report for Application No. 16847124.1, dated Feb. 26, 2019, 12 paqes.
European Examination Report for Application No. 16/847124.1 dated Dec. 8, 2020, 6 pages.
Chinese Patent Office, First Office Action, for Application No. 201680060877.7, dated Feb. 3, 2021, with Translation, 15 pages.

* cited by examiner

SENSOR DEVICE FOR BIOSENSING AND OTHER APPLICATIONS

CROSS-REFERENCE TO RELATED APPLICATIONS

The present application is a continuation application of U.S. Non-Provisional patent application Ser. No. 15/263,872 filed Sep. 13, 2016, which claims priority to and the benefit of U.S. Provisional Patent Application No. 62/220,119, filed Sep. 17, 2015, the disclosure of each of which is hereby incorporated by reference in its entirety as if fully set forth below and for all applicable purposes.

FIELD OF THE INVENTION

The present invention relates to generally to sensors, which may be utilized in the field of medical diagnostics and elsewhere. In particular, the present invention relates to a precision sensor configured to detect the presence of specific analytes. Exemplary analytes include enzymes, antibodies, proteins, and specific DNA or RNA sequences.

BACKGROUND

Biosensors provide new tools for diagnosing disease by allowing physicians to detect specific molecules in a biological sample. One type of biosensor includes one or more regions treated with a probe coating configured to detect specific molecules (i.e., analytes) by binding to the molecules and/or by reacting with them. In an exemplary sensor microarray, a set of different probe coatings are applied to different regions of a surface, such that specific probes are found at specific locations. The biological microarray is then exposed to an environment to be tested for the analytes. During this exposure, the biological probes react with their respective analytes provided they are present in the solution. The microarray may then be analyzed by measuring the quantity of analytes bound to the probes across the array. Because the probes are in defined locations within the array, individual analytes can be identified by their respective location even where the measurement technique could not otherwise tell them apart.

Despite their success, there are a number of concerns in biosensor development. For example, some biosensors may suffer from biofouling, the undesirable, non-specific binding of biological molecules to exposed areas of the biosensor. With repeated use, biofouling and/or contamination may degrade sensitivity as a best case and in the worst case may destroy a biosensor or require repeated cleaning to maintain the operation.

As another example, smaller microarrays on disposable platforms may require automated fluid handling or complex optical systems to apply, place, or grow each different biological probe onto its respective location on the surface during production. Further, conventional biological microarrays may also require high-precision fluidic systems and/or focused biosensors to detect the binding of analytes to each different biological probe location.

Conventional microarrays may also discourage customization. For mass-produced microarrays, it may simplify manufacturing to incorporate several or even hundreds of different probe-containing coatings, so that one microarray can be used in many applications. However, this may not allow a medical expert to configure a microarray for a specific situation, such as a protein-protein binding assay, a DNA/RNA detection assay, or a tumor marker assay. As a result, a care provider may perform a substantial number of tests in order to diagnose a single medical disorder. In other words, the microarray is usually a package deal.

As a final example, the detection method performed on the biosensor may require complex processing to measure analytes bound to the sensor including: tagging or labeling of particular analytes, Mass-Mass spectrometry, or amplification techniques such as polymerase chain reaction (PCR) to increase the amount of analyte. These methods add to the time and expense involved in the detection process.

Thus, while conventional biosensors and microarrays have been satisfactory in many aspects, the potential for significant improvements still remains.

SUMMARY

The present disclosure provides a sensor suitable for detecting specific analytes, a method for manufacturing the sensor, and a method for using the sensor in a diagnostic procedure to determine the presence of the analyte. In some embodiments, the sensor device includes a substrate, a dielectric layer disposed on the substrate, and a probe layer disposed on the dielectric layer. The probe layer is configured to react with an analyte. The reaction may include at least one of: binding with the analyte, undergoing a change in a chemical property of the probe layer, or undergoing a change in a structural property of the probe layer. In some such embodiments, an attribute of the dielectric layer is configured to identify the device during a process that determines whether the probe layer has reacted with the analyte. The attribute may include at least one of: a thickness of the dielectric layer, an index of refraction, a presence or absence of features, or a feature spatial pattern.

In some embodiments, a method is provided. The method includes exposing a sensor device to an environment to determine the presence of an analyte therein. The sensor includes a substrate, an identification structure disposed on the substrate, and a probe layer disposed on the identification structure and configured to undergo a reaction in the presence of the analyte. An inspection technique is performed on the sensor device to determine whether the probe layer has undergone the reaction. The inspection technique includes identifying the analyte by measuring a property of the identification layer. In some such embodiments, the inspection technique utilizes at least one of ellipsometry or scatterometry.

In further embodiments, a plurality of chips for medical diagnosis is provided. A first chip of the plurality includes: a substrate at a first end of the first chip, the substrate having a flat face having a length of from about 0.5 µm to about 5 mm; a probe layer at a second opposite end of the first chip, the probe layer of the first chip comprising a first biological probe capable of selectively reacting with a first analyte; and an identification layer disposed between the substrate and the probe layer of the first chip, the identification layer of the first chip comprising a material selected from the group consisting of dielectric material and non-dielectric material. A second chip of the plurality includes: a substrate at a first end of the second chip, the substrate comprising a flat face having a length of from about 0.5 µm to about 5 mm; a probe layer at a second opposite end of the second chip, the probe layer of the second chip comprising a second biological probe capable of selectively reacting with a second analyte; and an identification layer disposed between the substrate and the probe layer of the second chip, the identification layer of the second chip comprising a material selected from the group consisting of dielectric material and non-dielectric material. The first biological probe corresponds to the identification layer of the first chip, and the second biological probe corresponds to the identification layer of the second chip. The first biological probe and the second biological probe are different from each other, and the identification layer of the first chip and the identification layer of the second chip are optically distinguishable from each other.

In yet further embodiments, a method of detecting a medical condition is provided. The method includes providing a first chip and a second chip, exposing the first chip and the second chip to at least one analyte in solution, optically measuring in solution a first amount of a first analyte bound to the first chip and a second amount of a second analyte bound to the second chip, and distinguishing the first biological probe from the second biological probe by optically distinguishing a first identification layer of the first chip from a second identification layer of the second chip. The first chip includes: a substrate at a first end of the first chip, the substrate comprising a flat face having a length of from about 0.5 µm to about 5 mm; a probe layer at a second opposite end of the first chip, the probe layer of the first chip comprising a first biological probe capable of selectively reacting with a first analyte; and a first identification layer disposed between the substrate and the probe layer of the first chip, the first identification layer of the first chip comprising a material selected from the group consisting of dielectric material and non-dielectric material. The second chip includes a substrate at a first end of the second chip, the substrate comprising a flat face having a length of from about 0.5 µm to about 5 mm; a probe layer at a second opposite end of the second chip, the probe layer of the second chip comprising a second biological probe capable of selectively reacting with a second analyte, and a second identification layer disposed between the substrate and the probe layer of the second chip, the second identification layer of the second chip comprising a material selected from the group consisting of dielectric material and non-dielectric material.

Of course, it is understood that these embodiments are not limiting, and no particular feature is required for any particular embodiment.

BRIEF DESCRIPTION OF THE FIGURES

The present disclosure is best understood from the following detailed description when read with the accompanying figures. It is emphasized that, in accordance with the standard practice in the industry, various features are not drawn to scale and are used for illustration purposes only. In fact, the dimensions of the various features may be arbitrarily increased or reduced for clarity of discussion.

DETAILED DESCRIPTION

Figure 1:
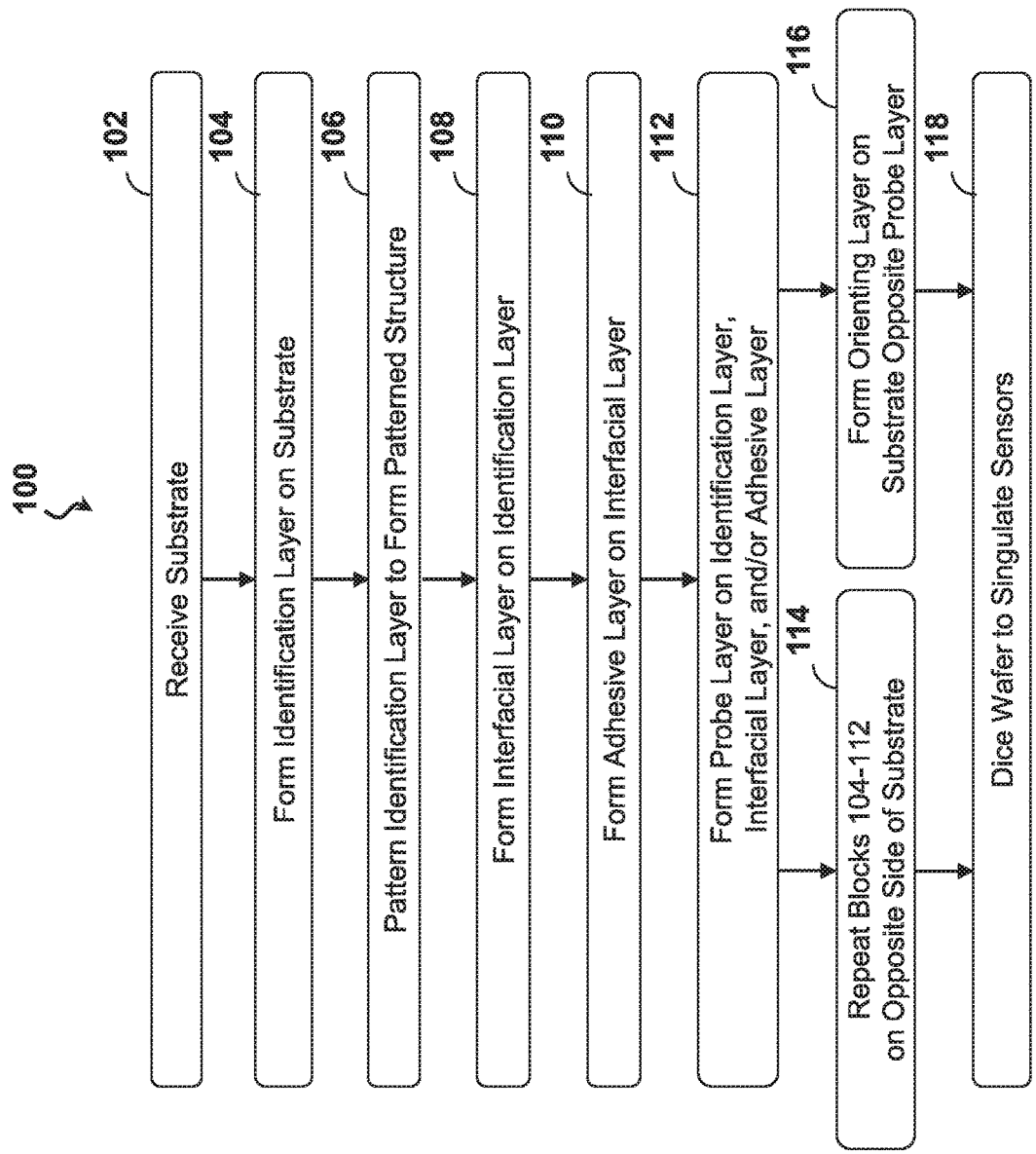
FIG. 1 is a flow diagram of a method of forming a sensing device according to aspects of the present disclosure.

The following disclosure provides many different embodiments, or examples, for implementing different features of the invention. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed unless otherwise noted.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. For example, if the device in the figures is turned over, elements described as being "below" or "beneath" other elements or features would then be oriented "above" the other elements or features. Thus, the exemplary term "below" can encompass both an orientation of above and below. The apparatus may be otherwise oriented (rotated 90 degrees or at other orientations) and the spatially relative descriptors used herein may likewise be interpreted accordingly.

Figure 2:
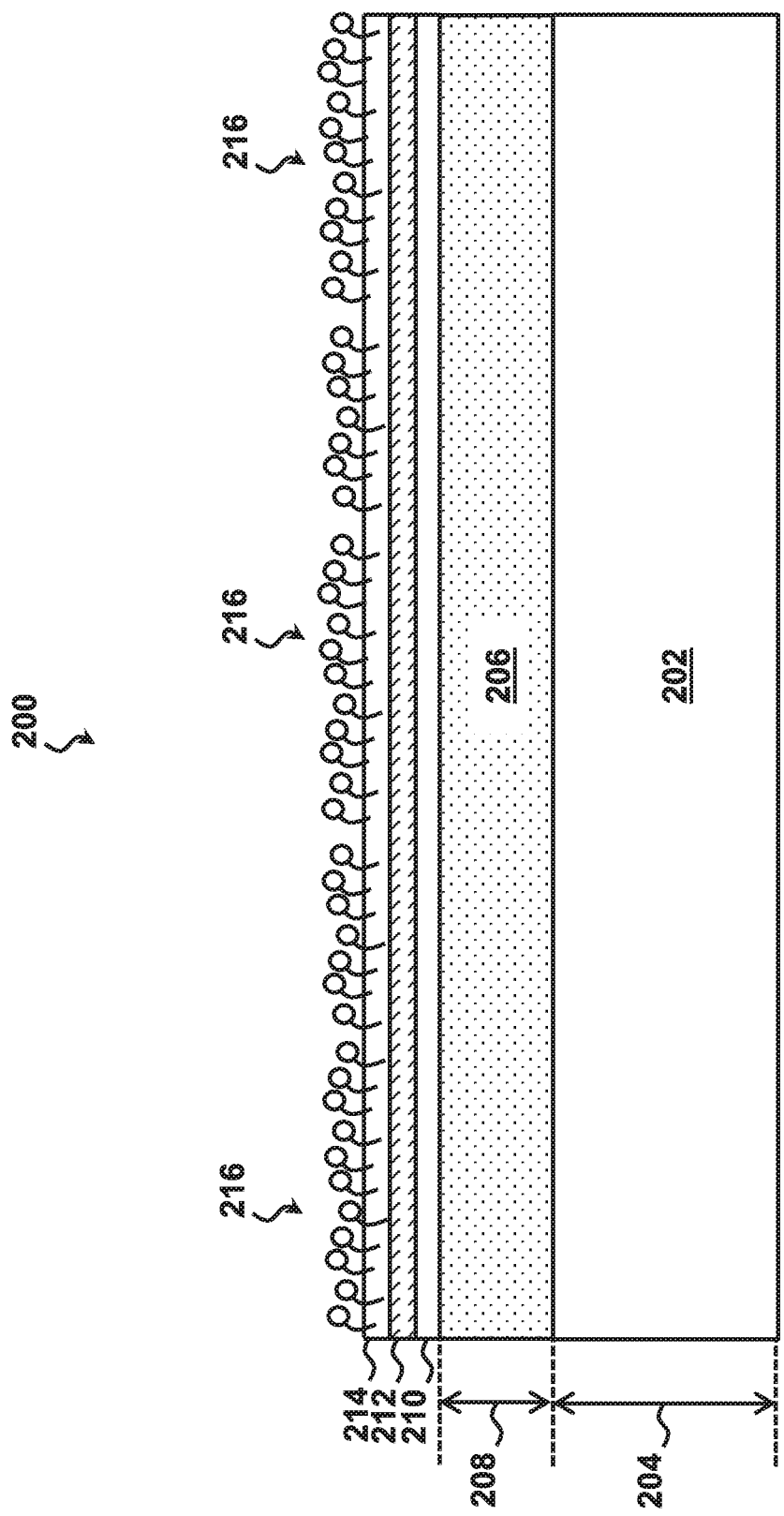
FIG. 2 is a cross-sectional view of a sensing device according to aspects of the present disclosure.
Figure 3:
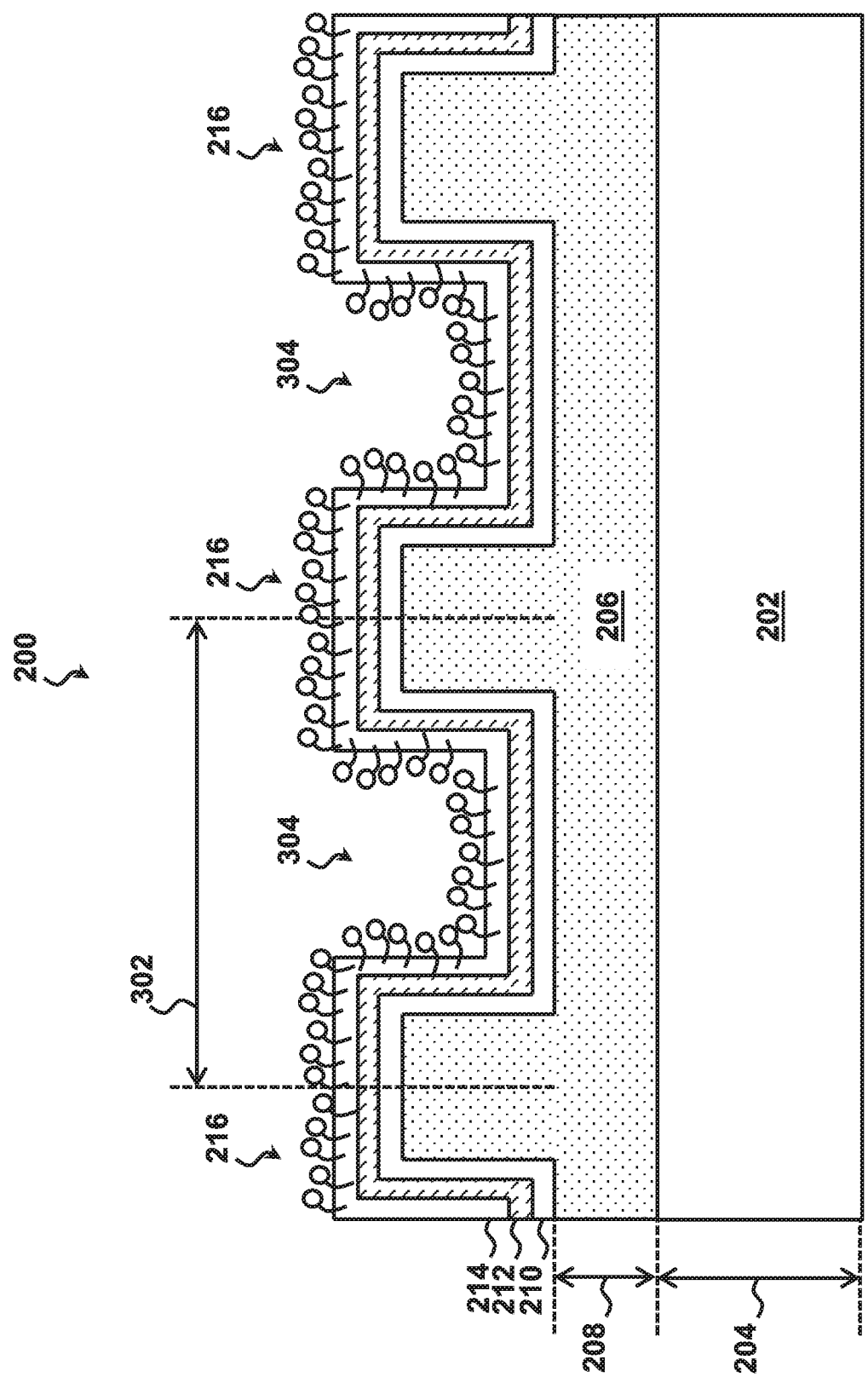
FIG. 3 is a cross-sectional view of a sensing device having identification features arranged at a first pitch according to aspects of the present disclosure.
Figure 4:
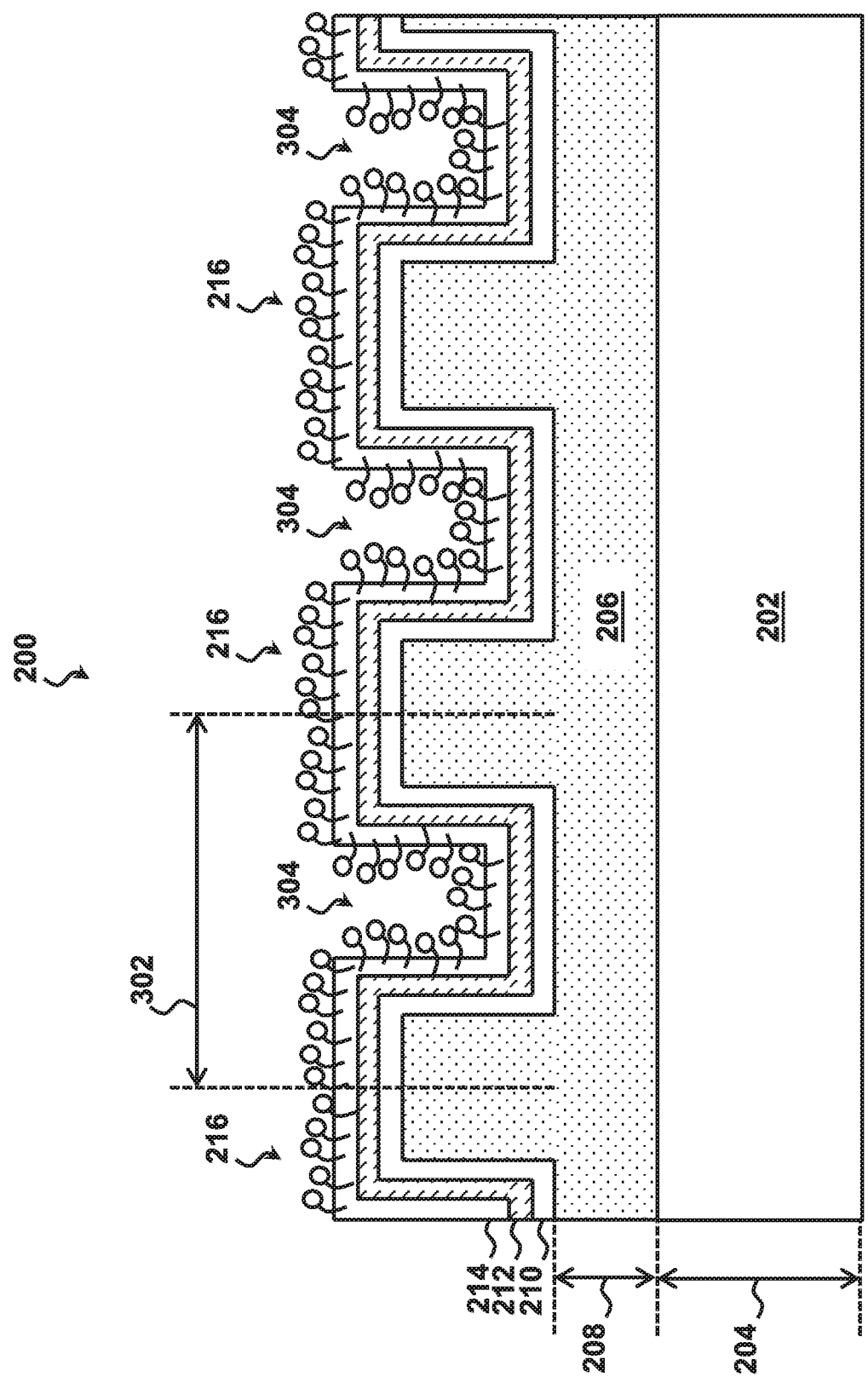
FIG. 4 is a cross-sectional view of a sensing device having identification features arranged at a second pitch according to aspects of the present disclosure.
Figure 5:
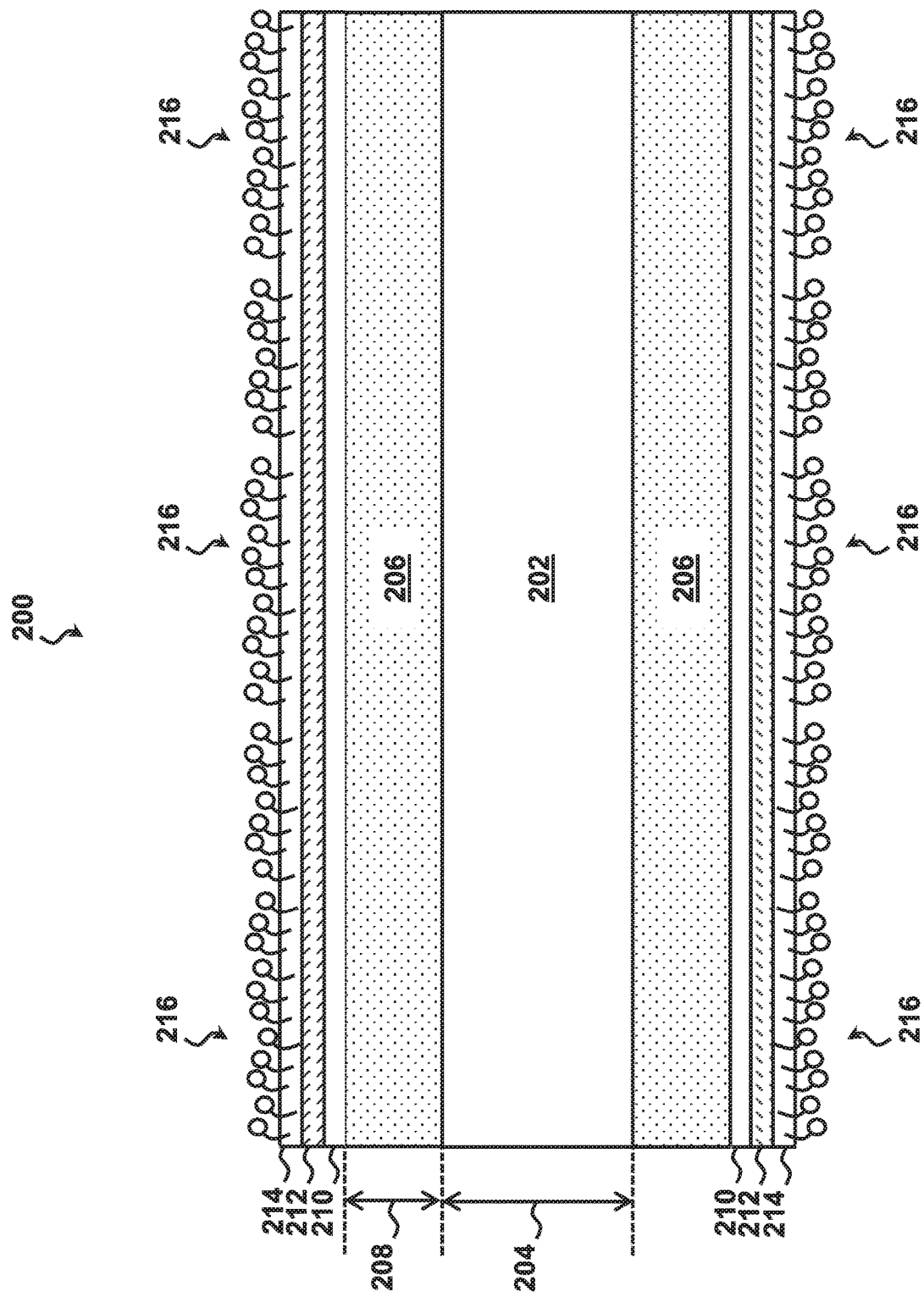
FIG. 5 is a cross-sectional view of the sensing device having probe layers disposed on multiple sides according to aspects of the present disclosure.
Figure 6:
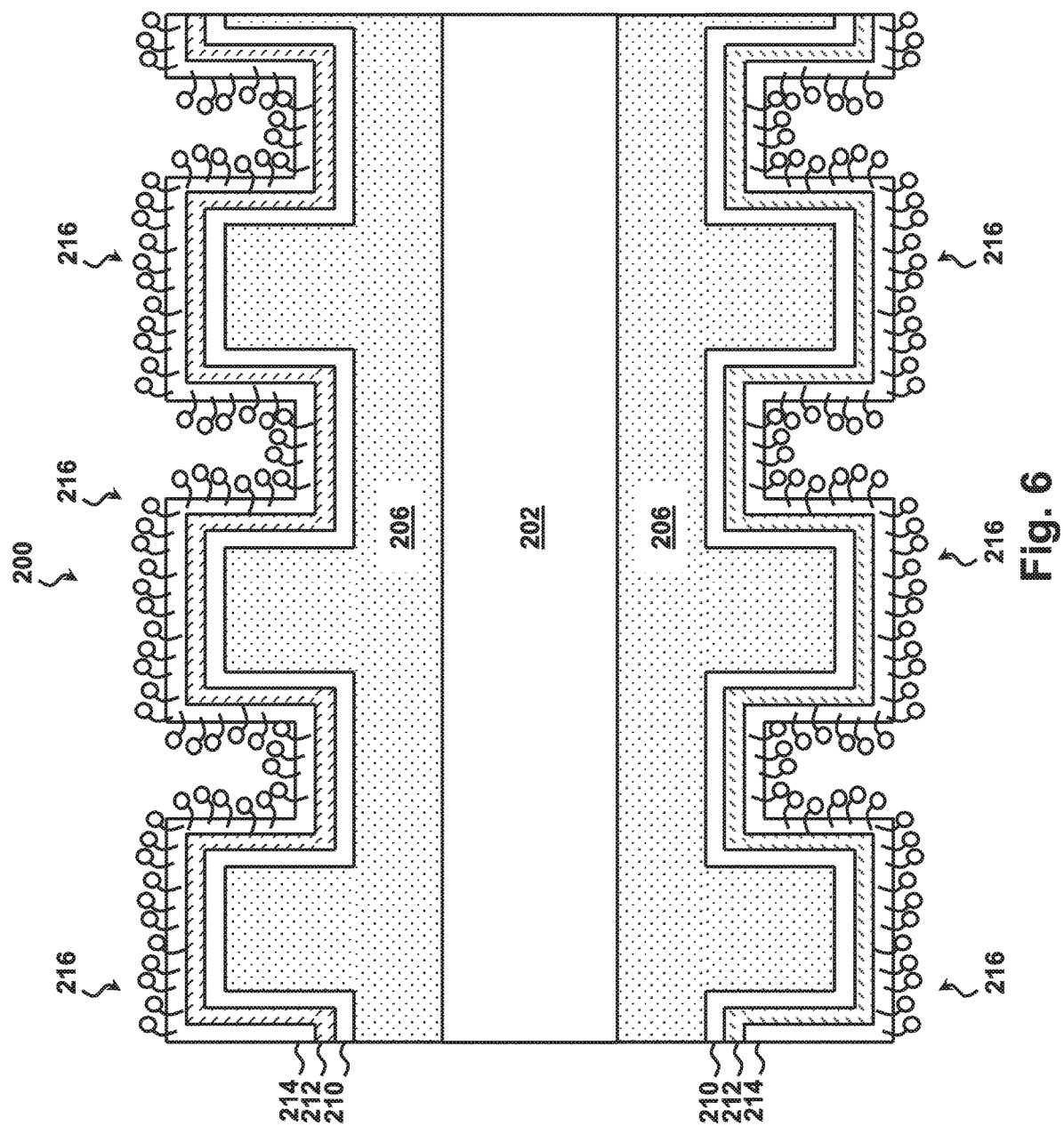
FIG. 6 is a cross-sectional view of the sensing device having identification features and probe layers disposed on multiple sides according to aspects of the present disclosure.
Figure 7:
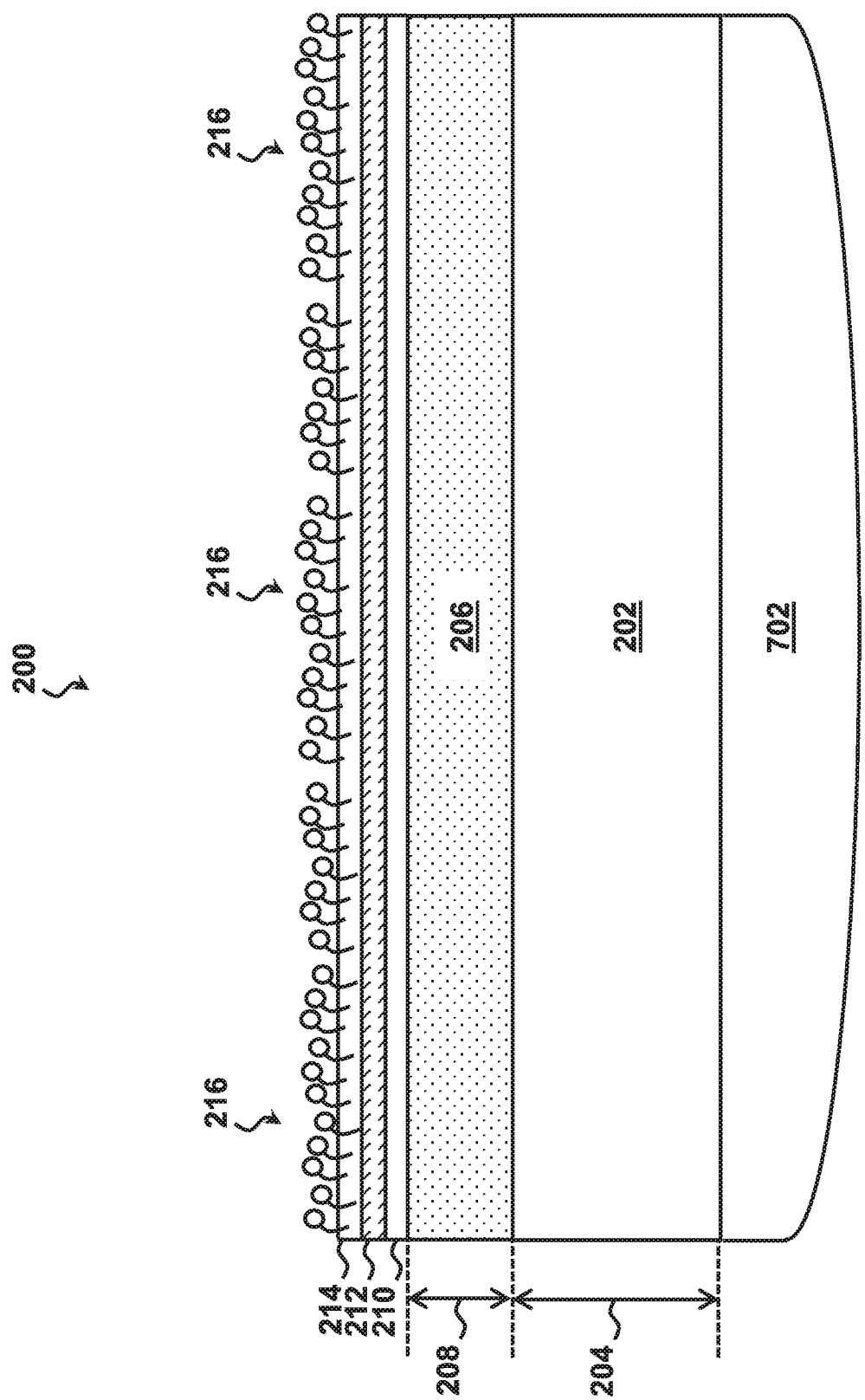
FIG. 7 is a cross-sectional view of the sensing device having an orienting feature according to aspects of the present disclosure.
Figure 8:
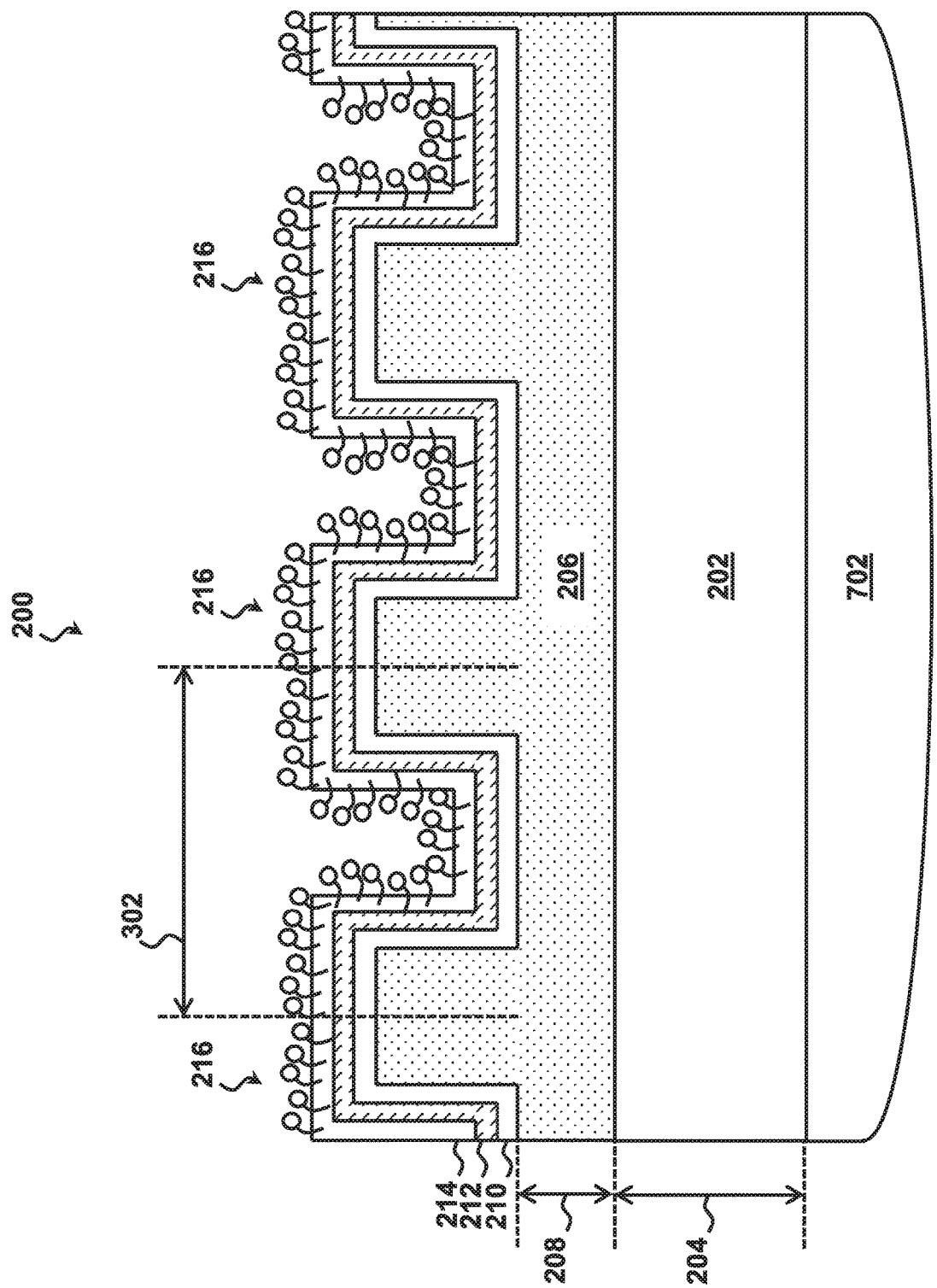
FIG. 8 is a cross-sectional view of the sensing device having identification features and an orienting feature according to aspects of the present disclosure.
Figure 9:
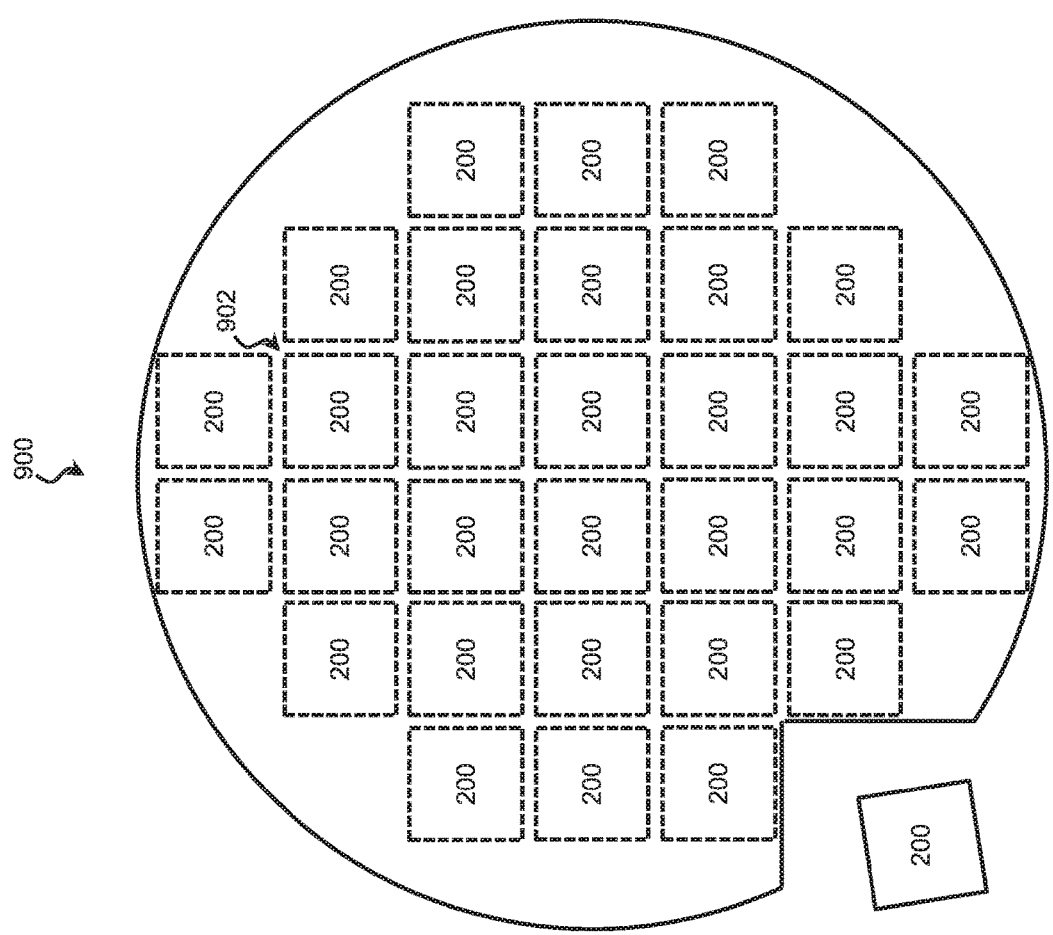
FIG. 9 is a top view of a wafer containing multiple sensors according to aspects of the present disclosure.

The present disclosure is directed to, but not otherwise limited to, a sensing device, such as a biosensor. The sensing device and a method of forming the device is described with reference to FIGS. 1-9. In that regard, FIG. 1 is a flow diagram of a method 100 of forming the sensing device (sensor) according to aspects of the present disclosure. It is understood that additional steps can be provided before, during, and after the method 100 and that some of the steps described can be replaced or eliminated for other embodiments of the method 100. FIG. 2 is a cross-sectional view of the sensing device 200 according to aspects of the present disclosure. FIG. 3 is a cross-sectional view of the sensing device 200 having identification features arranged at a first pitch or spatial pattern according to aspects of the present disclosure. FIG. 4 is a cross-sectional view of the sensing device 200 having identification features arranged at a second pitch or spatial pattern according to aspects of the present disclosure. FIG. 5 is a cross-sectional view of the sensing device 200 having probe layers disposed on multiple sides according to aspects of the present disclosure. FIG. 6 is a cross-sectional view of the sensing device 200 having identification features and probe layers disposed on multiple sides according to aspects of the present disclosure. FIG. 7 is a cross-sectional view of the sensing device 200 having an orienting feature according to aspects of the present disclosure. FIG. 8 is a cross-sectional view of the sensing device 200 having identification features and an orienting feature according to aspects of the present disclosure. For brevity, except where noted, the sensors 200 of FIGS. 2-8 are substantially similar, and descriptions that apply across FIGS. 2-8 will not be repeated for each figure. FIG. 9 is a top view of a wafer 900 containing multiple sensors 200 according to aspects of the present disclosure. For clarity and ease of explanation, some elements of the figures have been simplified.

Referring to block 102 of FIG. 1 and to FIG. 2, a substrate 202 is received, upon which other structures and materials may be disposed. The substrate 202 is exemplary of any supporting structure and accordingly may have any suitable structure and composition. For example, the substrate 202 may include an elementary (single-element crystalline) semiconductor, such as silicon and/or germanium; a compound semiconductor, such as silicon germanium; and/or a III-V semiconductor such as indium arsenide. Additionally or in the alternative, the substrate 202 may include a semiconductor oxide, a semiconductor nitride, a semiconductor carbide, a metal (e.g., aluminum, titanium, gold, iron, etc.), a metal oxide (e.g., $TiO_2$, $SiO_2$, $Al_2O_3$, etc.), a metal alloy (e.g., steel), and/or a polymer material (e.g., polyethylene terephthalate, polyimides, polyesters, polystyrenes, polyurethanes, etc.). The substrate 202 may also include materials such as fused silica, fused quartz, and/or soda-lime glass. The materials of the substrate 202 may be selected to be inert in aqueous solutions having a pH of from about 4 to about 12.

In these examples and others, the substrate includes one or more of: aluminum antimonide, aluminum arsenide, aluminum gallium arsenide, aluminum gallium indium phosphide, aluminum gallium nitride, aluminum gallium phosphide, aluminum indium arsenide, aluminum nitride, aluminum phosphide, beryllium telluride, bilayer grapheme, bismuth selenide, bismuth telluride, black silicon, boron arsenide, boron nitride, boron phosphide, cadmium arsenide, cadmium oxide, cadmium selenide, cadmium sulfide, cadmium telluride, cadmium zinc telluride, copper indium gallium selenide, copper zinc antimony sulfide, copper(I) oxide, copper(II) chloride, copper(II) oxide, crystalline silicon, diamond, gallium, gallium antimonide, gallium arsenide, gallium arsenide phosphide, gallium indium arsenide antimonide phosphide, gallium manganese arsenide, gallium nitride, gallium phosphide, gallium(II) selenide, germanene, germanium, grapheme, graphite, indium antimonide, indium arsenide, indium arsenide antimonide phosphide, indium gallium arsenide, indium gallium arsenide phosphide, indium gallium nitride, indium gallium phosphide, indium nitride, indium phosphide, indium(III) oxide, indium(III) sulfide, iron phosphide, iron(II,III) oxide, mica, phosphorene platinum silicide, pyrite, silicone, amorphous silicon, nanocrystalline silicon, polycrystalline silicon, porous silicon, strained silicon, silicon-germanium, silicon-tin, silver telluride, sulfoselenide, tin dioxide, tin telluride, tungsten disilicide, uranium dioxide, zinc oxide, zinc selenide, zinc sulfide, and zinc telluride.

The substrate 202 may be of any suitable size, and many factors may be considered in determining substrate size. In some exemplary embodiments, length and width may independently range between about 0.5 µm and about 5 mm (+/−10%). The length and width may be selected to aid in handling and measurement as well as to provide sufficient surface area for subsequent materials to be deposited. Likewise, the substrate 202 may have any suitable thickness (as indicated by reference 204) with some examples being between about 0.5 µm and about 100 µm (+/−10%). In some examples, the substrate 202 is small enough that the finished sensor 200 is suitable for in vivo applications where the sensor 200 circulates throughout the blood stream.

Referring to block 104 of FIG. 1, an identification layer 206 is formed on the substrate 202. The identification layer 206 allows the sensor 200 to be identified at various stages of a diagnostic procedure. As different types of sensors 200 may be configured to detect different analytes, it may be beneficial to be able to identify specific sensors 200 and/or sensor types in order to determine the corresponding analyte (s). This may be particularly beneficial in a procedure that utilizes multiple heterogeneous sensors 200 concurrently. In some embodiments, individual heterogeneous sensors 200 may be introduced into a sample, in vitro or in vivo, and afterwards, the identification layer 206 of each sensor 200 may be used to identify the nature of the sensor 200 and a corresponding analyte without the sensors 200 being bound onto an array. As described below, any suitable aspect of the identification layer 206 may be used to identify the sensor 200.

For example, in some embodiments, a thickness (as indicated by reference 208) of the identification layer 206 serves to identify the sensor 200. In some such examples, measurement of an analyte using the sensor 200 includes observing the sensor 200 using ellipsometry and/or scatterometry. Such techniques are explained in more detail below, but at a high level, both measure the optical effects of the sensor 200 in response to light or other electromagnetic radiation to determine whether the sensor 200 has reacted with an analyte. At the same time, ellipsometry and/or scatterometry may be used to measure the thickness of the identification layer 206. Accordingly, a specific thickness for the identification layer 206 may be selected to correspond to a particular analyte or class thereof. In a set of examples, it is determined that a difference in thickness of about +/−10 nm is readily distinguishable, and sensors 200 in these examples have identification layers 206 with thicknesses of about 10 nm, about 20 nm, about 30 nm, about 40 nm, about 50 nm, about 60 nm, about 70 nm, about 80 nm, about 90 nm, and about 100 nm, where each thickness corresponds to a particular probe layer material and analyte.

In some embodiments, the shape, structure, and/or composition of the identification layer 206 is selected so that the optical properties of the identification layer 206 serve to identify the sensor 200. In that regard, ellipsometry or scatterometry may be used to measure various optical properties of the identification layer 206 while determining whether the sensor 200 has reacted with an analyte. As ellipsometry can determine both thin film thickness and wavelength dependent optical properties, the identification layers 206 may be constructed of different materials and different thicknesses so that each specific identification layer 206 has an optical signature determined by the thickness and optical properties of its material that is uniquely identifiable among other identification layers 206 used together in one experiment. These optical properties may include an index of refraction, and accordingly in some embodiments, a specific index of refraction of the identification layer 206 may correspond to one or more analytes. In a set of examples, it is determined that a difference in index of refraction of about +/−0.2 is readily distinguishable, and sensors 200 in these examples have identification layers 206 with respective indices of refraction ranging from about 1.1 to about 2.9, wherein each index value corresponds to a particular probe layer material and analyte. In such embodiments, the index of refraction of the identification layer 206 may be selected so that the identification layer 206 is readily distinguishable from other materials in the sensor 200. Some optical properties, including index of refraction, may be wavelength dependent, and an identification layer 206 may have a unique property at some or all of wavelengths supported by the inspection tool.

Referring to FIG. 3, in some embodiments, the identification layer 206 has a set of patterned features that are identifiable by ellipsometry, scatterometry, or other suitable technique. Patterning of the identification layer 206 to form features is described below in the context of block 106. These features may be arranged in a periodic or aperiodic structure. For example, the identification layer 206 may include a nanostructured surface arranged in a periodic structure, such as a diffraction grating. The feature pitch 302 (centerline-to-centerline spacing) or other elements of the spatial pattern may be used to distinguish particular sensors 200. Accordingly, in a set of examples, it is determined that differences in the feature pitch 302 are readily distinguishable, and sensors 200 in these examples have identification layers 206 with feature pitches 302 selected to be between about 2 µm and about 190 nm (+/−10%). In the example, each feature pitch 302 corresponds to a particular probe layer material and corresponding analyte. Of course, thickness, optical response, and spatial pattern are only a few exemplary properties, and any suitable property of the identification layer 206 may be utilized to distinguish the sensor 200.

Regarding suitable materials, the identification layer 206 may include any suitable materials such as semiconductors, semiconductor dielectrics, metals, and/or metal oxides, and in various embodiments, the identification layer 206 includes silicon, germanium, silicon oxide, silicon nitride, silicon carbide, fused quartz, borosilicate glass, aluminum, titanium, gold, iron, strontium titanate, titanium dioxide ($TiO_2$), ZnO, $Al_2O_3$, polyethylene terephthalate, polyimides, polyurethanes, graphite, mica, and/or other suitable materials. The composition of the identification layer may be selected such that the identification layer 206 is inert to aqueous solutions having a pH from about 4 to about 12.

The identification layer 206 may be formed by any suitable technique. In one example, a semiconductor oxide-containing identification layer 206 is formed by performing a thermal process on a semiconductor substrate 202 in the presence of oxygen. The duration, temperature, pressure, atmospheric content, and/or other aspects of the thermal process may be selected to produce a desired thickness and composition of the identification layer 206. In further embodiments, the identification layer 206 may be formed by chemical vapor deposition (CVD), plasma-enhanced CVD (PECVD), physical vapor deposition (PVD), sputtering, atomic layer deposition (ALD), and/or other deposition suitable processes.

The identification layer 206 may also be configured to enhance measurement of the respective analyte. For example, the identification layer 206 may have different optical properties from an analyte-measuring material (e.g., a probe layer) of the sensor 200 to permit better accuracy when observing the analyte-measuring material. For example, the identification layer 206 may be configured to be absorptive at a wavelength that is used in the ellipsometric observation of the analyte-measuring material so that reflections from the identification layer 206 do not obscure the probe layer or any biological matter being measured.

Referring to block 106 of FIG. 1 and to FIG. 3, in some embodiments, the identification layer 206 may be patterned after deposition to define a plurality of features extending out from the bulk of the identification layer 206 and away from the substrate 202. These features may define an optical grating or other patterned structure. Suitable patterning techniques include photolithography, nanoimprinting, direct-write lithography, and/or other suitable techniques. In one embodiment, a photolithographic technique includes applying a photoresist coating on the identification layer 206, exposing portions of the photoresist to radiation (e.g., deep ultraviolet radiation), and developing the photoresist coating to leave either the exposed or unexposed portions of the resist. A partial thickness of the identification layer 206 is then etched using the remaining resist as a mask to protect underlying regions of the identification layer 206. Any suitable etching technique may be used including wet etching (e.g., KOH), dry etching, plasma etching, and reactive-ion etching. In some embodiments, the etching technique is orientation dependent (anisotropic) to avoid undercutting the resist. The remaining photoresist may be removed after the etching.

As described above, the patterned identification layer 206 may be used to identify a probe layer material and the corresponding analyte being measured. The pattern may also be used to increase the selectivity of the sensor 200. In that regard, the desired analyte may be competing with non-specific binding of other molecules or particles to a probe layer formed on the outermost surface of the sensor 200. However, if a trench 304 between features of the patterned identification layer 206 is sufficiently small, it may filter out compounds other than the analyte of interest from binding with the portion of the probe layer within the trench 304. While the desired analyte and the larger particles compete to bind at the topmost surface, within the trenches 304, the analyte can bind to the walls unhindered by the larger particles. Accordingly, in some embodiments, the feature pitch 302 of the patterned identification layer 206 is configured so that the resulting trench in the finished sensor 200 filters out analytes larger than the analyte of interest. Referring to FIG. 4, a sensor 200 is shown that is substantially similar to that of FIG. 3, except that the feature pitch 302 is smaller and configured to block larger analytes from the trench 304.

Referring to block 108 of FIG. 1 and to FIGS. 2-4, in some embodiments, an interfacial layer 210 is formed on the identification layer 206 in order to facilitate bonding of subsequent materials. The interfacial layer 210 may include any suitable material including suitable semiconductors, dielectrics, metals, metal oxides, metal alloys, and/or polymers. In various examples, the interfacial layer includes $SiO_2$, $TiO_2$, and/or $Al_2O_3$. The interfacial layer 210 may be formed by any suitable technique including thermal oxidation, CVD, PECVD, PVD, ALD, and/or sputtering, and may be formed to any suitable thickness, with exemplary thicknesses ranging from about 1 µm to about 2 nm. The composition of the interfacial layer 210 may be selected to avoid interfering with measurement of the identification layer 206 or any other material of the sensor 200.

Referring to block 110 of FIG. 1, and to FIGS. 2-4, in some embodiments, an adhesive layer 212 is formed on the identification layer 206 and interfacial layer 210, if present. The adhesive layer 212 may include one or more molecules having one or more functional groups that are capable of tethering a probe material to a layer of the chip, such as the identification layer 206 or the interfacial layer 210. For example, 3-aminopropyl trimethoxysilane has an amine group and a siliane group and may be included in the adhesive layer 212 in order to functionalize the identification layer 206 and/or interfacial layer 210 with an amine group. Subsequent materials with a reactive group, such as an epoxide ring, may react with the amine group to adhere to the sensor 200. Other suitable materials for the adhesive layer 212 include 3-glycidoxypropyltrimethoxysilane and related molecules.

Referring to block 112 of FIG. 1, and to FIGS. 2-4, a probe layer 214 or other analyte-measuring layer is formed on the identification layer 206. In embodiments that include an interfacial layer 210 and/or adhesive layer 212, the probe layer 214 may be disposed directly on and physically contacting the interfacial layer 210 or the adhesive layer 212. Furthermore, in embodiments in which the identification layer 206 is patterned to include features and trenches 304 defined therebetween, at least a portion of the probe layer 214 is disposed within the trenches 304 on the vertical side surfaces and the horizontal bottom surface.

The probe layer 214 may be configured to selectively react with one or more specific analytes. These reactions may include bonding to the analyte as well as undergoing a chemical and/or structural change, such as a molecular refolding, without necessarily bonding to the analyte. Accordingly, the probe layer 214 may include reaction sites 216 (enlarged for clarity) configured for reacting with and/or binding to the analyte. According to several exemplary embodiments, the probe layer 214 includes one or more reaction sites 216 that are capable of selectively binding to or reacting with an analyte at a ratio of specific to non-specific binding of about 10:1 to about 1000:1. Suitable materials for inclusion at the reaction site 216 include biotin (which is known to react with avidin, streptavidin, and neutravidin), various antibodies (which are known to reach to specific antigens), antibody antigen complexes, chromatin, interleukins, enzymes, and/or proteins. Furthermore, the probe layer 214 may include strands of DNA and/or RNA at the reaction sites 216 in order to bind with complementary strands of DNA and/or RNA. In this way, the sensor 200 may include DNA and RNA probes operable to identify and measure specific nucleotide sequences. Accordingly, in various embodiments, the probe layer 214 includes a specific strand of DNA having from about 10 to about 150 bases, a specific strand of RNA having from about 10 to about 150 bases, an enzyme, an antibody, and/or a protein, each operable to selectively react in the presence of an analyte.

Because of the small size of the sensor 200, in some embodiments, it may be difficult to orient individual sensors 200 within a group so that they lay flat, do not overlap, and have their probe layers 214 directed towards the measuring apparatus. For example, orienting the sensors 200 after exposure may include dispersing the sensors 200 on a flat surface either still in an aqueous solution or after drying. They may be manipulated into an array by various methods including: automated visual identification followed by pick and place, or the use of microfluidics and designed slots that capture the sensors 200. The sensors 200 may also be simply dispersed randomly on a flat surface where their location could be determined by automated optical inspection. Of course, there are many techniques of taking randomly distributed micro objects and orienting them in known configurations in both fluid and ambient air environments.

However, in some embodiments, orientation issues can be avoided by simple redundancy so that given sufficient sensors 200, a ~50% reduction in sensors 200 being measured would be acceptable. In other embodiments, orientation issues are addressed by repeating the process of blocks 104-112 of FIG. 1 on an opposite side of the substrate 202 as shown in block 114 of FIG. 1 and FIGS. 5 and 6. In this manner, regardless of the orientation, a probe layer 214 of the sensor 200 will be right side up. The sensors 200 of FIGS. 5 and 6 are substantially similar to those of FIGS. 2 and 4, respectively, except that a second identification layer 206 and a second probe layer 214 are formed on a second surface of the substrate 202 opposite the substrate surface upon which the first identification layer 206 and first probe layer 214 are formed. A second interfacial layer 210 and/or adhesive layer 212 may also be formed between the second identification layer 206 and the second probe layer 214.

Referring to block 116 of FIG. 1 and to FIGS. 7 and 8, orientation issues may also be addressed by forming an orienting layer 702 on the substrate 202 opposite the identification layer 206 and probe layer 214. In that regard, the sensors 200 of FIGS. 7 and 8 are substantially similar to those of FIGS. 2 and 4, respectively, except that an orienting layer 702 is formed on a second surface of the substrate 202 opposite the substrate surface upon which the identification layer 206 and the probe layer 214 are formed. The orienting layer 702 may facilitate sensor manipulation when the sensor 200 is being exposed to analytes and afterwards when the sensor 200 is being examined. Any suitable property of the orienting layer 702 may be used to orient the sensor 200. In some embodiments, the shape of the orienting layer 702 is configured to cause the probe layer 214 to align in a given orientation in a fluid and/or air environment. In some embodiments, a material affinity of the orienting layer 702 is configured to cause the probe layer 214 to align in a given orientation relative to another surface. For example, the orienting layer 702 may be hydrophilic, hydrophobic, and/or magnetic. Accordingly, the orienting layer 702 may include any suitable material, such as a semiconductor, a semiconductor dielectric, a metal, a metal oxide, and/or a polymer, and may be formed by any suitable process.

Referring to block 118 of FIG. 1 and to FIG. 9, at any time during the method 100, the sensor 200 may be singulated from other sensors 200. In that regard, multiple sensors 200 may be manufactured concurrently on a single wafer 900. The singulation process separates the sensors 200 from one another and from the remainder of the wafer 900. To facilitate singulation, the wafer 900 may include scribe lines 902, sacrificial areas intended to be used during the dicing process. Accordingly, in an embodiment, a diamond saw is run down the scribe lines 902 to separate the sensors 200. The scribe lines 902 are large enough to minimize damage caused to the sensors 200 by the saw. Additionally or in the alternative, etching and/or mechanical force may be used to separate the sensors 200.

Figure 10:
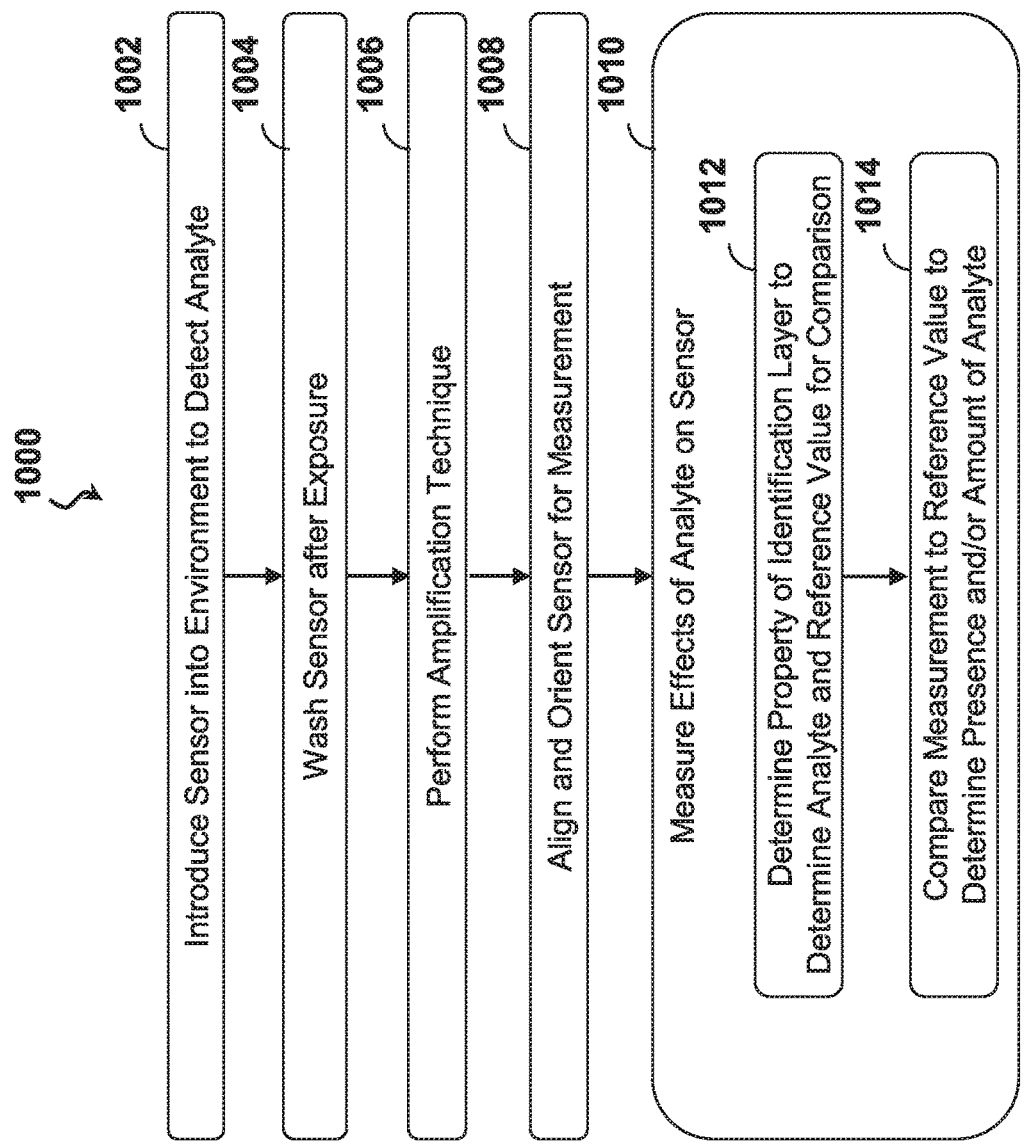
FIG. 10 is a flow diagram of a method of determining the presence of an analyte according to aspects of the present disclosure.

A diagnostic technique utilizing the sensor 200 is described with reference to FIG. 10. In that regard, FIG. 10 is a flow diagram of a method 1000 of determining the presence of an analyte according to aspects of the present disclosure. It is understood that additional steps can be provided before, during, and after the method 1000 and that some of the steps described can be replaced or eliminated for other embodiments of the method 1000.

Referring to block 1002 of FIG. 10, a sensor 200, such as the sensor 200 of any of the embodiments described with reference to FIGS. 1-9, is introduced to an environment to determine whether it contains an analyte of interest. The sensor 200 includes a probe layer 214 that is configured to undergo a change in property in the presence of the analyte. For example, the probe layer 214 may bind to the analyte and/or may experience a chemical or structural change in response to the analyte. The sensor 200 is suitable for use in vivo or in vitro. In an in vivo example, the sensor 200 is introduced to the blood stream to determine the presence of the analyte therein. In an in vitro example, the sensor 200 is introduced into a prepared solution containing fragmented DNA and/or RNA to determine the presence of a particular sequence. Biological samples can be prepared for analysis using any suitable technique. For example, cells can be lysed and their contents can be separated by centrifugation, chromatography, filtering, and other suitable methods. The sensor 200 may remain exposed to the environment for any suitable amount of time, and an ambient temperature during the exposure may be controlled to promote a reaction between the probe layer 214 and the analyte. In an example, the sensor 200 is exposed to the environment at room temperature for at least an hour.

Referring to block 1004 of FIG. 10, after exposure, the sensor 200 may be washed using a solution selected to remove contaminants without disrupting the effects of the reaction between the probe layer 214 and the analyte. For example, the solution may be selected to avoid removing analytes bonded to the probe layer 214. In one such embodiment, the sensor 200 is washed using a hybridization buffer and allowed to dry.

Referring to block 1006 of FIG. 10, an amplification technique may be performed in order to make the analyte or the response of the probe layer 214 more detectable. For example, polymerase chain reaction (PCR) may be used to increase the length of a single strand DNA analyte before or after the single strand of DNA is bound to the probe layer 214. In this way, the thickness of the layer of DNA to be measured can be increased. Other suitable amplification techniques include analyte labeling and analyte tagging.

Referring to block 1008 of FIG. 10, the sensor 200 is oriented and aligned for measurement of the probe layer 214. The sensor 200 may be aligned while in an aqueous solution or after drying. Individual sensors 200 may be manipulated by various methods including automated visual identification followed by pick and place and the use of microfluidics and designed slots that capture the sensors 200. In some embodiments an orientation feature 702 of the sensor 200 is used to align and orient the sensor 200.

Referring to block 1010 of FIG. 10, the sensor 200 is inspected using any suitable technique such as ellipsometry and/or scatterometry to determine the effect of the analyte upon the sensor 200, if any. In an example, the sensor 200 is illuminated with narrow or broad-spectrum light (including visible light, infrared radiation, ultraviolet radiation, deep ultraviolet radiation, etc.) from one or more angles. The light reflected or diffracted from the identification layer 206, interfacial layer 210, adhesive layer 212, probe layer 214 and/or the analyte bound thereto is collected and analyzed. In this manner, the intensity, polarization, and/or other properties may be measured to determine various aspects of the sensor 200.

Referring to block 1012 of FIG. 10, the inspection of the sensor 200 may include determining a property of light reflected by the identification layer 206. Based on the measured property of light, a property of the identification layer 206, such as thickness, index of refraction, presence or absence of features, feature pattern, etc., is determined that indicates the type of the sensor 200, the composition of the probe layer 214, and/or the analyte to which the sensor 200 reacts. In this way, individual sensors 200 may be identified from among a collection of heterogeneous sensors 200.

Referring to block 1014 of FIG. 10, the inspection of the sensor 200 may include determining a property of light reflected by the probe layer 214 and/or analyte and comparing it to a reference taken from a reference sensor 200. As the sensor 200 may be manufactured to a very high accuracy, the difference between the measured property and the reference should be substantially due to the effects of the analyte on the probe layer 214 and/or due to any analyte still remaining on the probe layer 214. The optical properties of the sensor 200 materials are consistent enough to be modeled as invariant values, and this consistency contributes to the accuracy and precision of the measurements. To improve throughput, in some embodiments, the analysis of block 1014 may be performed using the same data as the identification of block 1012 without taking further measurements.

In an example using ellipsometry, the thickness of the adhesive layer 212, probe layer 214, and any analyte bound to the probe layer is determined and compared to a negative reference value that corresponds to the thickness of the adhesive layer 212 and the probe layer 214 and/or a positive reference value that corresponds to the thickness of the adhesive layer 212 and a saturated probe layer 214. The exact references value may be determined based on the identification of block 1012. Any difference between the measurements may be due primarily to the thickness of the analyte bound to the probe layer 214 or physical changes to the probe layer 214 caused by the analyte. In this way, the presence of the analyte can be determined. In addition to a binary presence detection, the amount of change may also be used to determine a relative abundance of the analyte in the environment.

In an example using scatterometry, the three-dimensional structure of the adhesive layer 212, probe layer 214, and any analyte may be determined. This three-dimensional structure may be compared to a negative (analyte free) reference or a positive (analyte saturated) reference to determine those changes that are due to the presence of the analyte. The reference model may be determined based on the identification of block 1012. In addition to a binary presence detection, the amount of change between the measured sensor 200 and the reference may also be used to determine a relative abundance of the analyte in the environment. Scatterometry can measure changes in thickness of the layers on the sidewalls independently from the changes on the top of the grating structure. This may be used to increase the selectivity of the sensor 200. In that regard, the desired analyte may be competing with non-specific binding of other molecules or particles to the probe layer 214. As discussed above, in some embodiments, the spacing between features of the identification layer 206 create narrow trenches 304 that filter out compounds other than the analyte of interest that may bond with the probe layer 214. While the desired analyte and the larger particles compete to bind to the top of the grating walls, within the trenches 304, the analyte can bind to the walls unhindered by the larger particles. Accordingly, in some embodiments, the inspection of block 1014 focuses on probe layer 214 and analyte measurements on the vertical side surfaces and/or the horizontal bottom surfaces inside the trenches 304.

In this way, the present disclosure provides a sensor 200 suitable for measuring particular analytes, a method 100 for manufacturing the sensor 200, and a method 1000 for using the sensor 200 in a diagnostic procedure to determine the presence of the analyte. The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method comprising:
   performing at least one of ellipsometry or scatterometry on a sensor device to obtain data associated with a presence of an analyte, wherein the sensor device includes:
      a substrate;
      an identification structure disposed on the substrate; and
      a probe layer disposed on the identification structure and configured to undergo a reaction in the presence of the analyte;
   determining a property of the identification structure based on the data;
   determining a type of the probe layer based on the determined property of the identification structure; and
   determining the presence of the analyte based on the data and the determined type of the probe layer.

2. The method of claim 1, wherein the property includes at least one of: a thickness of the identification structure, a presence or absence of a feature, or a feature spatial pattern.

3. The method of claim 1, wherein performing at least one of ellipsometry or scatterometry comprises performing scatterometry, wherein the sensor device further includes an orientation feature disposed on the substrate opposite the identification structure, the method further comprising aligning the sensor device using the orientation feature.

4. The method of claim 1, wherein determining whether the probe layer has undergone the reaction comprises determining whether the probe layer has performed at least one of: binding with the analyte, undergoing a change in a chemical property of the probe layer that is identifiable as a change in optical properties, or undergoing a change in a structural property of the probe layer.

5. The method of claim 4, wherein the change in the structural property of the probe layer comprises a change in a thickness of the probe layer.

6. The method of claim 1, wherein the identification structure comprises a dielectric layer, and wherein the sensor device further comprises an adhesive layer disposed on the dielectric layer.

7. The method of claim 6, wherein the sensor device further comprises an interfacial layer disposed between the dielectric layer and the probe layer.

8. The method of claim 1, wherein the identification structure comprises an aluminum oxide layer.

9. The method of claim 1, wherein the sensor device comprises a first chip, wherein the analyte comprises a first analyte, and wherein the method further comprises:
   performing the at least one of ellipsometry or scatterometry on a second chip, the second chip comprising a substrate, an identification structure disposed on the substrate, and a probe layer disposed on the identification structure and configured to undergo a reaction with a second analyte; and
   determining a property of the identification structure of the second chip based on the data;
   determining a type of the probe layer of the second chip based on the determined property of the identification structure of the second chip; and
   determining the presence of the second analyte based on the data and the determined type of the probe layer of the second chip.

10. The method of claim 9, wherein the identification structures of the first and second chips independently comprise a dielectric layer having an index of refraction of from about 1.1 to about 2.9 and a thickness of from about 2 nm to about 3 µm.

11. The method of claim 10, wherein a difference between the index of refraction of the dielectric layer of the first chip and the index of refraction of the dielectric layer of the second chip is at least ±0.2.

12. The method of claim 10, wherein a difference between the thickness of the dielectric layer of the first chip and the thickness of the dielectric layer of the second chip is at least ±2 nm.

13. A method for determining a presence of analytes, comprising:
   providing a first sensor chip comprising:
      a first substrate;
      a first identification structure disposed on the first substrate, the first identification structure comprising a first thickness; and
      a first probe layer disposed on the first identification structure and configured to undergo a reaction with a first analyte;
   providing a second sensor chip comprising:
      a second substrate;
      a second identification structure disposed on the second substrate, the second identification structure comprising a second thickness different from the first thickness; and
      a second probe layer disposed on the second identification structure and configured to undergo a reaction with a second analyte;
   performing ellipsometry on at least one of the first sensor chip or the second sensor chip to obtain data;
   determining, based on the data, an identification structure thickness measurement;
   determining whether the first sensor chip or the second sensor chip is present based on the identification structure thickness measurement; and
   determining whether the first analyte or the second analyte has reacted with the first probe layer or the second probe layer based on:
      the data; and
      the determination of whether the first sensor chip or the second sensor chip is present.

14. The method of claim 13, wherein the first identification structure comprises an aluminum oxide layer.

15. The method of claim 13, wherein the first identification structure comprises a first dielectric layer and the second identification structure comprises a second dielectric layer.

16. The method of claim 15, wherein each of the first dielectric layer and the second dielectric layer comprises an index of refraction of from about 1.1 to about 2.9 and a thickness of from about 2 nm to about 3 µm.

17. The method of claim 16, wherein a difference between the index of refraction of the first dielectric layer and the index of refraction of the second dielectric layer is at least ±0.2.

18. The method of claim 16, wherein a difference between the thickness of the first dielectric layer and the thickness of the second dielectric layer is at least ±2 nm.

\* \* \* \* \*